(12) United States Patent
Nakamura et al.

(10) Patent No.: US 7,704,530 B2
(45) Date of Patent: Apr. 27, 2010

(54) ANTIMICROBIALLY TREATED MATERIAL AND METHODS OF PREVENTING COLORING THEREOF

(75) Inventors: Kenji Nakamura, c/o Taiki Awaji Factory, 3-41 Nishiawaji 6-chome, Higashi Yodogawa-ku, Osaka-shi, Osaka (JP); Koji Nakamura, c/o Taiki Awaji Factory, 3-41 Nishiawaji 6-chome, Higashi Yodogawa-ku, Osaka-shi, Osaka (JP)

(73) Assignees: Kenji Nakamura, Osaka (JP); Koji Nakamura, Osaka (JP)

( * ) Notice: Subject to any disclaimer, the term of this patent is extended or adjusted under 35 U.S.C. 154(b) by 255 days.

(21) Appl. No.: 10/237,827

(22) Filed: Sep. 10, 2002

(65) Prior Publication Data

US 2003/0157176 A1    Aug. 21, 2003

(30) Foreign Application Priority Data

Sep. 14, 2001  (JP) .............................. 2001-280377
Oct. 2, 2001   (JP) .............................. 2001-305987
May 17, 2002   (JP) .............................. 2002-142353
Jul. 18, 2002  (JP) .............................. 2002-209914

(51) Int. Cl.
   A61K 33/38    (2006.01)
   A61K 31/52    (2006.01)
   A01N 43/54    (2006.01)
   A01N 43/90    (2006.01)
   A01N 59/16    (2006.01)

(52) U.S. Cl. ............... 424/618; 514/263.1; 514/263.35; 514/263.4; 514/256

(58) Field of Classification Search ................. 424/670, 424/618; 514/263.1, 263.4, 263.35, 256, 514/366, 394, 396, 397, 399, 401, 402, 495
See application file for complete search history.

(56) References Cited

U.S. PATENT DOCUMENTS 5,122,418 A * 6/1992 Nakane et al. ............... 424/401
6,183,763 B1 * 2/2001 Beerse et al. ............... 424/404
7,125,570 B2 * 10/2006 Taniguchi et al. ........... 424/604

FOREIGN PATENT DOCUMENTS

| DE | 0 406 657 A1 | | 1/1991 |
|---|---|---|---|
| EP | 0 732 052 A2 | | 9/1996 |
| EP | 0 834 253 A2 | | 4/1998 |
| EP | 1 066 825 A1 | | 1/2001 |
| GB | 1297258 A | * | 11/1972 |
| JP | 06-287315 | | 10/1994 |
| JP | 07-97480 | | 4/1995 |
| JP | 08027848 A | * | 1/1996 |
| JP | 08-71124 | | 3/1996 |
| JP | 08-169981 | | 7/1996 |
| JP | 09-104765 | | 4/1997 |
| JP | 09-183707 | | 7/1997 |
| JP | 2000016904 A | * | 1/2000 |
| WO | WO 00/53413 | | 9/2000 |

OTHER PUBLICATIONS

File CAPLUS, STN/CAS online, Acc. No. 1975:592095, Doc. No. 83:192095 (DeMember et al., Journal of the American Chemical Society (1975), vol. 97, No. 21, pp. 6240-6245), Abstract.*
Wikipedia (http://en.wikipedia.org/wiki/Sphericity)(2006), pp. 1, 2.*

* cited by examiner

*Primary Examiner*—Johann R Richter
*Assistant Examiner*—Nathan W Schlientz
(74) *Attorney, Agent, or Firm*—Knobbe Martens Olson & Bear, LLP

(57) ABSTRACT

The present invention is an antimicrobially-treated material which has a coloring preventing function and is in contact with water or moisture or contains water, comprising (A) a silver-based antimicrobial agent which dissociates silver ions in the water system and (B) a silver ion trapping agent for trapping silver ions comprising one or more kinds of compounds selected from the group consisting of purine bases, pyrimidine bases, thiabendazole, and potassium iodide, wherein a ratio of (A)/(B) is 1/1 to 100/1 by weight.

7 Claims, No Drawings

ANTIMICROBIALLY TREATED MATERIAL AND METHODS OF PREVENTING COLORING THEREOF

BACKGROUND OF THE INVENTION

1. Field of the Invention

The present invention relates to antimicrobially treated material containing silver-based antimicrobial agents having a coloring preventing function, in particular to plastic compositions and various products using thereof, external skin agents, wet tissues and paste-type cosmetics. Furthermore, the present invention relates to methods of preventing coloring of antimicrobially treated material which have a coloring preventing function and contain silver-based antimicrobial agents.

In more detail, the present invention relates to products such as containers and packaging materials made with antimicrobial plastic compositions which have a coloring preventing function and comprise silver-based antimicrobial agents, bases of nucleic acid components, thiabendazole, and the like.

Further, the present invention relates to external skin agents and sheet-like cosmetics having a coloring preventing function which comprise silver-based antimicrobial agents and at least one or more kinds of components selected from purine bases, free bases thereof and thiabendazole.

2. Description of the Related Art

The antimicrobial effect of silver zeolite has been known for a long time (Patent No. 128654: "A method of producing hard water softening agent having an antimicrobial activity" filed by the Taiwan Institute of Invention in Aug. 12, 1937). Admixing of silver-based antimicrobial agents with various products and treatment of various products with silver-based antimicrobial agents have been generally practiced.

As the demand for silver-based antimicrobial agents expands, the silver-based antimicrobial agents have been actively developed, and a number of technical reports related to the production and use of such antimicrobial agents have been published (Japanese Patent Application Laid-open No. 1984-133235; Japanese Patent Application Laid-open No. 1985-100504).

Although silver-based antimicrobial agents are useful antimicrobial agents, a problem that products are undesirably colored upon application of these silver-based antimicrobial agents is getting a great deal of attention. Accordingly, technology for preventing coloring of products, in which the silver-based antimicrobial agents is used, is now under study. For example, a method for partially exchanging zeolite with ammonium ions has been proposed (Japanese Patent Application Laid-open No. 1988-265958; Japanese Patent Application Laid-open No. 1989-24860).

However, when silver-based antimicrobial agents are admixed with plastics or the like using such technology, the content of containers is occasionally colored due to the effect of silver ions although coloring of the plastics can be prevented to some extent. Furthermore, residual coloring and color development are big problems when an aqueous medium containing silver-based antimicrobial agents is retained in a carrier and used for wiping or when cosmetics containing silver-based antimicrobial agents are directly applied to the skin. For example, when an aqueous medium containing silver-based antimicrobial agents was retained in sheet bases such as paper or nonwoven cloth, the silver-based antimicrobial agents remaining after use adhered to the skin, clothes or the like and colored yellow to brown, which was hard to prevent.

Further, residual coloring and color development caused a problem even when silver zeolite antimicrobial agents were directly added to cosmetics or directly admixed with sheet bases without using an aqueous medium.

Characteristically, silver-based antimicrobial agents have a broad antimicrobial histograph to bacteria and fungi, are effective to various kinds of bacteria, are safe to a human body, do not generate resistant microorganisms, and are safe in terms of environmental pollution. Accordingly, their use in wet products, such as external skin agents and sheet-like cosmetics, and paste-type products used, for example, in caring babies, seniors or the like and in cosmetics are expected. However, in actuality, the coloring problem has been a bottleneck in use in products that have direct contact with the skin, such as cosmetics, since silver-based antimicrobial agents undesirably color the skin and clothes brown or yellow due to residual coloring or coloring of the silver-based antimicrobial agents themselves, as mentioned above.

In the field of cosmetics, silver-based antimicrobial agents have an excellent effect in preventing underarm and body odor, are also effective against acne bacteria, and can be used safely on the body. In particular, their use in wet tissues and paste-type cosmetics, such as deodorants, is promising. Useful pocket products are also expected.

However, as mentioned above, silver-based antimicrobial agents cause a serious coloring problem when cosmetic sheet-like wet products are made by soaking nonwoven cloth with an admixture of silver-based antimicrobial agents and an aqueous medium. Accordingly, methods of using silver zeolite antimicrobial agents in cosmetic products without undesired coloring have been in demand.

The present inventors directed their attention to the fact that while silver ions dissociated in water exhibit a remarkable antimicrobial effect when silver-based antimicrobial agents are placed under moist conditions, the silver ions are associated or oxidized to color yellow to brown, that the extent of such coloring depends on the amount of silver ions present in the water system, and that the amount of silver ions dissociated and released from the silver-based antimicrobial agents in the water system greatly changes under the influence of ions of salts and the like present in the water system.

The present inventors tried to solve the problem caused by using silver-based antimicrobial agents in producing cosmetics without undesired coloring when the silver-based antimicrobial agents are admixed with an aqueous medium to produce products such as external skin agents. As a result, it was revealed that when silver-based antimicrobial agents were admixed with external skin agents in cosmetics or the like, the degree of coloring by silver ions dissociated from the silver-based antimicrobial agents is greatly affected by the admixed components or air contained in the admixture so that the amount of silver ions dissociated and released from the silver-based antimicrobial agents in the water system had to be controlled in order to prevent the coloring since the prevention was occasionally difficult.

It was also revealed that when silver zeolite antimicrobial agents were admixed with sheet-like cosmetics, the coloring by silver ions was greatly affected by cosmetic components, components of nonwoven cloth used as a sheet base or air contained so that the amount of silver ions dissociated and released from the silver zeolite antimicrobial agents in the water system had to be controlled in order to prevent the coloring since the prevention was difficult and the influence of the silver ions was greater than that of the cosmetic components.

Accordingly, the present inventors tried to solve the problem caused by using silver zeolite antimicrobial agents in producing cosmetic sheet-like wet products without undesired coloring when the silver zeolite antimicrobial agents are admixed with an aqueous medium and nonwoven cloth was soaked in the admixture.

On the other hand, Japanese Patent Application Laid-open No. 1989-164722 proposes compositions as means for preventing coloring caused by silver, in which a UV absorbent is added to silver zeolite. However, no coloring prevention effect in containers and packaging materials could be attained since the coloring is caused also by the action of liquid components in the containers other than UV light. Japanese Patent Application Laid-open No. 1988-265958 and Japanese Patent Application Laid-open No. 1989-24860 propose antimicrobial resin compositions having a coloring prevention function in which exchangeable ions are partly or totally substituted with ammonium ions and silver ions. However, the color prevention effect is insufficient and in particular, containers for aqueous fluids are markedly colored. In Japanese Patent Application Laid-open No. 1991-145410, coloring by UV rays is prevented by incorporating amine silver complex ion into zeolite soaked in an ammonium ion solution.

Silver-related coloring is occasionally caused by a reaction of liquid components in containers other than light and no effective means is so far available to prevent such coloring. For example, Japanese Patent Application Laid-open No. 1991-181538 proposes compositions effective to weather-resistant coloring, in which silver zeolite, a hindered amine compound and a neutralizing agent are incorporated into a polyolefin resin containing a chlorine compound. According to this proposal, polymethylpropyl-3-oxy[4-tetramethylpiperidyl]siloxan is preferable as a hindered amine compound. However, coloring of containers and packaging materials caused by liquid contents was not sufficiently prevented using such compounds.

Conventionally, in antimicrobial plastic packaging products containing silver-based antimicrobial agents, particularly in plastic containers and packaging materials used for cosmetic products containing liquid components as the contents, coloring caused by a reaction between the liquid contents and silver ions incorporated into the packaging containers could not be prevented and thus it was difficult to contain aqueous substances such as cosmetic lotions in containers which contain silver-based antimicrobial agents.

SUMMARY OF THE INVENTION

Accordingly, an object of the present invention is to provide antimicrobially-treated material without problems caused by residual coloring and color development in antimicrobially-treated material containing silver-based antimicrobial agents. In particular, an object of the present invention is to provide containers and packaging materials using plastic compositions containing silver-based antimicrobial agents, which cause no undesired coloring with liquid contents in the containers and packaging materials. Further, an object of the present invention is to provide various products produced using plastic compositions containing silver-based antimicrobial agents. Further, an object of the present invention is to provide external skin agents containing silver-based antimicrobial agents, which cause no problematic residual coloring or color development. Further, an object of the present invention is to provide sheet-like cosmetics containing silver-based antimicrobial agents, which cause no problematic residual coloring or color development. Further, an object of the present invention is to solve problems caused by coloring when silver-based antimicrobial agents are directly added to cosmetic products. Further, an object of the present invention is to provide methods of preventing coloring in the abovementioned antimicrobially-treated material.

The present invention solved the abovementioned conventional problems according to the following basic components.

The first embodiment of the present invention is an antimicrobially-treated material, which has a coloring preventing function and is in contact with water or moisture or contains water, comprising (A) a silver-based antimicrobial agent which dissociates silver ions in the water system and (B) a silver ion trapping agent for trapping silver ions comprising one or more kinds of compounds selected from the group consisting of purine bases, pyrimidine bases, thiabendazole, and potassium iodide, wherein a ratio of (A)/(B) is 1/1 to 100/1 by weight.

The second embodiment of the present invention is an antimicrobial plastic composition having a coloring preventing function, which comprises (A) a silver-based antimicrobial agent and (B) one or more kinds of compounds selected from the group consisting of purine bases, pyrimidine bases, thiabendazole, and potassium iodide.

The third embodiment of the present invention is an antimicrobial plastic container having a coloring preventing function, wherein the antimicrobial plastic composition in the second embodiment described above is arranged in the whole container or on the outer surface or inner surface of the container by an in-mold forming or surface treatment.

The fourth embodiment of the present invention is an antimicrobial plastic packaging material having a coloring preventing function, wherein the antimicrobial plastic composition in the second embodiment described above is arranged in one or more layers of a single-layer or multiple-layer film.

The fifth embodiment of the present invention is an antimicrobial plastic brush having a coloring preventing function, wherein the antimicrobial plastic composition in the second embodiment described above is a brush made of synthetic fiber.

The sixth embodiment of the present invention is antimicrobial plastic fiber having a coloring preventing function, wherein the antimicrobial plastic composition in the second embodiment described above is synthetic fiber.

The seventh embodiment of the present invention is an external skin agent having a coloring preventing function, which comprises (A) a silver-based antimicrobial agent and (B) one or more kinds of compounds selected from the group consisting of purine bases, pyrimidine bases, thiabendazole, and potassium iodide.

The eighth embodiment of the present invention is a sheet-like cosmetic having a coloring preventing function, wherein (A) a silver-based antimicrobial agent and (B) one or more kinds of compounds selected from the group consisting of purine bases, pyrimidine bases, thiabendazole, and potassium iodide are retained in a sheet base with an aqueous medium. Other than the abovementioned liquid medium, dental fluids, toothpastes, powders, pressed powders, haircare agents and the like can also be used.

The ninth embodiment of the present invention is a method of preventing coloring of an antimicrobially-treated material having contact with water or containing water, in which (A) a silver-based antimicrobial agent which dissociates silver ions in the water system and (B) a silver ion trapping agent comprising one or more kinds of compounds selected from the group consisting of purine bases, pyrimidine bases, thiabendazole, and potassium iodide are mixed at a ratio of (A)/(B)=1 to 100 by weight.

As mentioned above, when silver zeolite is admixed as an antimicrobial agents in external skin agents such as cosmetics and silver ions are dissociated from the silver-based antimicrobial agent, a silver ion concentration range which exhibits an antimicrobial effect and a silver ion concentration range which causes coloring are overlapped. Accordingly, the coloring could not be avoided to maintain the antimicrobial effect. The present inventors therefore intensively studied the cause of such coloring with silver zeolite. As a result, they found that when silver-based antimicrobial agents were admixed with external skin agents or cosmetics, marked coloring was caused, for example, by (1) dissociation of silver ions resulting in oxidation or association of silver when admixed with an aqueous medium and (2) dissolved oxygen or air when admixed with an aqueous medium and retained in sheet bases such as nonwoven cloth. It was also found that the coloring was caused by (3) the interaction between cosmetic components and silver zeolite, for example, in combined use of aluminium chlorohydrate, which is commonly used as an antiperspirant, and silver zeolite or (4) a reaction of silver zeolite with the sweat of the human body.

The present inventors then revealed that the degree of coloring was most marked in (2) and accordingly coloring caused by (1) as well as by (3) and (4) was effectively prevented when the coloring caused by (2) was prevented, and thus completed the present invention.

Techniques of the present invention to prevent the most marked coloring caused by (2) as mentioned above will be explained as follows.

A basic idea of the present invention for preventing coloring of silver zeolite is to make an purposeful use of the concentration rages of silver ions dissociated from silver zeolite in water system, i.e., a concentration range A which is effective for antimicrobial action and a concentration range B which is responsible for coloring.

Namely, the concentration range A which is effective for antimicrobial action is more than 1 ppm that is the antimicrobially effective concentration of silver ions while the concentration range B which is responsible for coloring is 40 ppm or more, so that a concentration range C for silver ions dissociated in the water system, which is effective for antimicrobial action without causing coloring, exists between 1 ppm and 40 ppm (preferably between 5 ppm and 30 ppm).

The concentration range of silver ions dissociated from 1000 ppm silver zeolite in the water system varies from 40 ppm to 600 ppm. This variation is probably due to a decrease in the silver ion concentration caused by generation of silver oxide or adsorption of silver ions in the water system, or is under the influence of the degree of dissociation of silver ions by metal salts, surfactants, and temperature. Therefore, the amount of silver ions decreases and an antimicrobial effect cannot be sustained even if the silver ion concentration is set within the range C by controlling the amount of silver substitution or the amount of silver zeolite to be used.

In the abovementioned range B which is responsible for coloring, the degree of coloring is greater in sheet bases such as nonwoven cloth or paper than in liquid alone in the water system, which naturally requires coloring prevention measures. Undesired coloring could be prevented by maintaining the amount of silver ions within the range C in which no coloring by silver ions occurs if silver ions in the range B which is responsible for coloring can be chemically trapped from the range A which is effective for antimicrobial action. In other words, no coloring will occur and antimicrobial action will be effective by maintaining the concentration of dissociated silver ions within the range C in which silver ions have an antimicrobial effect without coloring. The silver ion concentration can be controlled within the range C by decreasing the amount of silver substitution or reducing the amount of antimicrobial agents to be used. However, ultimately, an antimicrobial effect cannot be attained in this case since the decrease in silver ions with time or due to change in the system cannot be complemented.

Weak adsorption is preferable to trap silver ions in the abovementioned concentration range B in which coloring occurs. In order to sustain an antimicrobial effect, it is important that when silver ions in the intermediate range C, in which dissociated silver ions cause no coloring, are consumed, the trapped silver ions are released to complement silver ions in the abovementioned range C. Thus, the original antimicrobial effect of silver-based antimicrobial agents will be reduced if the trapping is through bonds highly reactive with silver in the silver-based antimicrobial agents, such as strong bonds to mask SH groups.

Silver ions exhibit no antimicrobial effect or, if any, the effect is unsustainable in the range A in which silver ions cause no coloring. On the other hand, silver ions exhibit a marked antimicrobial effect but cause coloring in the range A with an increased silver ion concentration. As mentioned above, an antimicrobial effect by silver ions is sustained and coloring is controlled by adding purine bases, pyrimidine bases or thiabendazole even when silver ions are increased (range A). Namely, purine bases or the like can loosely form complexes with silver ions, maintain the silver ion concentration in a certain range, and sustain the silver ion concentration within the range C.

In the present invention, examples of appropriate compounds for trapping silver ions to satisfy the abovementioned conditions include purine bases and pyrimidine bases, in particular at least one component selected from free bases and purine bases or pyrimidine bases of components of DNA, RNA or the like. Further, the coloring prevention is significantly improved by admixing thiabendazole with silver-based antimicrobial agents.

Additionally, in the present invention, the same effect also can be obtained by using potassium iodide as compounds for trapping silver ions.

According to the present invention, it was revealed that coloring caused by silver ions could be prevented by using an admixture as a silver ion trapping agent, which comprises components selected from purine bases or pyrimidine bases of nucleic acid components, free bases thereof and thiabendazole at a ratio of 1 to 100 parts (preferably 10 to 80 parts, more preferably 30 to 60 parts) by weight to 100 parts by weight of silver-based antimicrobial agents and that this coloring prevention was also markedly effective in the most serious coloring caused by the abovementioned cause (2) (in sheet-like cosmetics with an aqueous medium). It was also revealed that the coloring could be prevented by additionally using aluminium chlorohydrate which is commonly used as an antiperspirant and that this coloring prevention is effective also in contact with sweat of the human body.

The abovementioned basic phenomena for coloring prevention are not restrictedly applied to sheet-like cosmetics with an aqueous medium and the coloring prevention is similarly effective in general cosmetics containing silver-based antimicrobial agents. Further, the coloring prevention is similarly effective when silver-based antimicrobial agents and the abovementioned silver ion trapping agents are directly admixed with materials for nonwoven cloth or paper to compose sheet bases or directly admixed with porous materials to compose sheet bases.

Further, use as a substitute for paraben in cosmetics is also possible.

An antimicrobial plastic composition or a external skin agent of the present invention uses (A) 100 parts by weight of a silver-based antimicrobial agent and (B) one or more kinds of silver ion trapping agents selected from the group consisting of purine bases or pyrimidine bases, free bases thereof, and thiabendazole at a ratio of 1 to 100 parts by weight, preferably 10 to 80 parts by weight, more preferably 30 to 60 parts by weight, to 100 parts by weight of the silver-based antimicrobial agent.

Coloring prevention effect can not be attained when the ratio of silver ion trapping agents is less than 1 part by weight to 100 parts by weight of a silver-based antimicrobial agent because trapping of silver ions in the abovementioned concentration range B, in which coloring occurs, is insufficient. Further, silver ions in the intermediate range C in which dissociated silver ions cause no coloring are also trapped when the ratio of the abovementioned silver ion trapping agents exceeds 100 parts by weight, which undesirably decreases an antimicrobial effect. Accordingly, use of 1 to 100 parts by weight is most effective.

In an antimicrobial plastic composition of the present invention, a silver-based antimicrobial agent and silver ion trapping agents are used preferably at a ratio of 0.05 to 5.0% by weight, more preferably 0.10 to 3.0% by weight, relative to 100% by weight of a plastic preform. An antimicrobial effect cannot be attained when the ratio is less than 0.05% by weight. Furthermore, there is no further increase in the antimicrobial effect when the ratio exceeds 5.0% by weight, so that the use of more than 5.0% is uneconomical.

Further, in an external skin agent of the present invention, a silver-based antimicrobial agent and silver ion trapping agents are used preferably at a ratio of 0.01 to 10.0% by weight, more preferably 0.10 to 3.0% by weight, to 100% by weight of the external skin agent. An antimicrobial effect cannot be attained when the ratio is less than 0.01% by weight. Furthermore, there is no further increase in the antimicrobial effect when the ratio exceeds 10.0% by weight.

In a sheet-like cosmetic of the present invention, an aqueous medium is integrated at a ratio of 50 to 300% (more preferably 100 to 300%) by weight to 100% by weight of a sheet base. The aqueous medium preferably contains an admixture comprising (1) 100 parts by weight of a silver-based antimicrobial agent and (2) 1 to 100 parts by weight of one or more compounds selected from the abovementioned purine bases or pyrimidine bases or free bases thereof and thiabendazole.

The abovementioned silver-based antimicrobial agent can be used at a ratio of 0.02 to 3.0% by weight, preferably 0.02 to 1.0% by weight, more preferably 0.03 to 0.5% by weight, to 100% by weight of a sheet base. An antimicrobial effect cannot be attained when the ratio is less than 0.02% by weight. Further, the antimicrobial effect can be sufficiently attained when the ratio is up to 1.0% by weight and there is no further increase in the antimicrobial effect when the ratio exceeds 1.0% by weight.

Appropriate silver ion trapping agents used with a silver-based antimicrobial agent used in a sheet-like cosmetic of the present invention are compounds selected from purine bases or pyrimidine bases of nucleic acid components, compounds of free bases thereof and thiabendazole. Silver ion trapping agents can be used at a ratio of 1 to 100 parts by weight, preferably 10 to 80 parts by weight, more preferably 30 to 60 parts by weight, to 100 parts by weight of the silver-based antimicrobial agent. When the ratio is less than 1 part by weight to 100 parts by weight of the silver-based antimicrobial agent, silver ions in the abovementioned concentration range B in which coloring occurs cannot be sufficiently trapped so that coloring prevention cannot be attained. Further, when the abovementioned ratio of the silver ion trapping agents exceeds 100 parts by weight, silver ions in the intermediate range C in which no coloring occurs with dissociated silver ions are also trapped so that the antimicrobial effect is undesirably decreased. Accordingly, the effect is most appropriately attained at a ratio of 1 to 100 parts by weight.

The abovementioned ratio of the silver ion trapping agents to the silver-based antimicrobial agent is the same when the sheet-like cosmetic is the cosmetic itself.

Examples of purine bases or pyrimidine bases used as the abovementioned silver ion trapping agents include compounds having free bases and RNA or DNA components, i.e., adenine, guanine, cytosine, thymine, and uracil.

Thiabendazole or the like can be used as a silver trapping agent which exhibits a similar coloring preventing effect. When heat tolerance is required in polymer molding, pyrimidine bases are preferable to purine bases and thiabendazole is most preferable.

In the present invention, the abovementioned coloring preventing agent used in a aqueous medium can be any agent generally used in aerosols, powders, pressed powders, creams, and the like. In particular, coloring prevention is markedly effective in external skin agents such as underarm deodorants, talcum powders, hair tonics, toothpastes, bath agents, toiletries (e.g., shampoos, rinses, cosmetics, milky lotions, and soaps), rectal cleansing agents, lady's cleansing agents, and wet tissue-type and paste-type cosmetic products in which unwoven cloth or paper is used as a sheet base.

External skin agents containing a silver zeolite antimicrobial agent feel rough and occasionally unpleasant to the skin depending on the site of application. This is because crystals of zeolite are cubic. In order to dissolve this unpleasantness and to attain pleasantness, powdery particles having a sphericity of 40 or more (preferably 60 or more) are used at a ratio of 10 to 1000 parts by weight, preferably 20 to 800 parts by weight, to 100 parts by weight of the silver zeolite antimicrobial agent. In order to dissolve the roughness to the skin caused by the surface roughness of zeolite in external skin agents containing a silver zeolite antimicrobial agent, powdery fine particles having a sphericity of 40 or more, which can be obtained from the reflective sphericity using a microscope, are effectively used. Fine globular powdery particles to be used have a diameter of 1 to 40 µm and an average diameter of 3 to 20 µm, and can be porous solid particles or hollow capsule-like particles having a porous exterior. The abovementioned fine globular powdery particles are used at a ratio of 10 to 1000 parts by weight to 100 parts by weight of the silver zeolite antimicrobial agent in external skin agents.

If the ratio is less than 10 parts by weight, smoothing effect on cubic zeolite crystals cannot be attained because the amount of the fine particles is insufficient to dissolve the roughness. Further, use of 1000 parts by weight, namely exceeding 10 times the amount of the silver-based antimicrobial agent, is not preferable because the original property of the agent as an external skin agent is lost.

In the present invention, an admixture of 2 to 3 components comprising (A) a silver-based antimicrobial agent, (B) silver ion trapping agents such as purine bases and pyrimidine bases and preferably (C) globular powdery particles having a sphericity of 40 or more is used at a ratio of 0.01 to 10.0% by weight, preferably 0.1 to 3.0% by weight, in total in an external skin agent.

Materials for fine globular powdery particles can be organic or inorganic, insoluble in water and excellent in their absorbability and moisture retainability. Examples of the inorganic materials include metal silicates such as calcium silicate, magnesium silicate, and aluminium silicate; metal carbonates such as calcium carbonates and cobalt carbonate;

metal oxides such as cobalt oxide and ion oxide; metal hydroxide such as ion oxide hydrate. Further, organic materials can be appropriately formed in fine globular particles of synthetic resins. For example, calcium carbonate powder is poured into a monomer solution, the resulting admixture is stirred to form globular beads, for example, by pearl polymerization, and then the globular beads obtained are immersed in an acid solution to elute and remove the calcium carbonate powder to obtain the final bead product.

Examples of silver-based antimicrobial agents used in the present invention for preventing coloring include silver zeolite (Zeomic: registered trademark, Sinanon Co., Ltd.; Bactekiller: registered trademark, Kanebo), silver apatite (Apasider: registered trademark, Sangi Co. Ltd.), silver phosphate zirconium (Novaron: registered trade mark, Toagosei Co., Ltd.) silver glass (Antimicrobial Composite Glass: registered trademark, Koa Glass Co., Ltd.), and inorganic coating silver oxide (Microfree AMP): registered trademark, Dupont).

The amount of silver ions contained in silver-based antimicrobial agents can be different depending on the kind of the silver-based antimicrobial agents used. However, it is preferably 0.5 to 3.0% by weight, more preferably 1.0 to 2.0% by weight.

In the present invention, the abovementioned compounds effective to prevent coloring can prevent, for example, coloring of silver zeolite in the water system; coloring caused by cosmetic components and silver zeolite, for example, coloring caused by various aluminium compounds which are commonly used as an antiperspirant, such as aluminium chlorohydrate, and silver zeolite; and coloring caused by sweat and silver zeolite. They are effective in aqueous media, such as purified water, deodorant lotions, body lotions, and facial lotions, and also in aerosols, powders, creams, and lotions. In particular, the coloring prevention is markedly effective in wet tissues, and paste-type cosmetics in which the compounds are retained in sheet bases such as nonwoven cloth and paper.

In case where a sheet-like cosmetic of the present invention is a wet tissue, an admixture of a silver-based antimicrobial agent and the abovementioned silver ion trapping agents is homogeneously dispersed in an aqueous medium, and the resulting liquid composition is infiltrated into a sheet base such as nonwoven cloth and paper at a ratio of 100 to 300% by weight (preferably 150 to 250% by weight), after which the product is airtightly packaged.

In case where a sheet-like cosmetic of the present invention is a paste-type cosmetic, gel is made by admixing a macromolecular tackiness agent admixed with a moisture retaining agent and, if necessary with vitamin C, with a silver-based antimicrobial agent and the abovementioned silver ion trapping agents and then applied on or infiltrated into a sheet base such as woven cloth, knitted materials and nonwoven cloth to make a product. After infiltration, airtight packaging is necessary similarly to the case of the wet tissue. The abovementioned paste-type cosmetics are useful to cleanse the skin by pasting them on the face and body and are additionally effective for acne prevention, beautification and deodorization. The products can be used safely without damaging the skin or clothes since the paste-type products themselves cause no coloring. Thus, it becomes possible to commercially provide paste-type products with silver zeolite antimicrobial agents for the first time.

An external skin agent of the present invention can be safely and hygienically used in products such as underarm deodorants, talcum powders, hair tonics, toothpastes, bath agents, toiletries (e.g., shampoos, rinses, lotions, creams, milky lotions, and soaps), rectal cleansing agents, and lady's cleansing agents, maintaining its original antimicrobial effect without coloring.

An external skin agent of the present invention is effective in particular for prevention of underarm and body odor and is also effective in removing bad breath and preventing dental caries and pyorrhea alveolaris in oral use and in preventing pneumonia of bedridden patients. In bathing use, the agent is effective in removing germs in bathing water and for safety of skin. As mentioned above, the rough feeling caused by cubic crystals of zeolite or the like can be ameliorated to attain smooth feeling to the skin by using fine globular powdery particles with a silver-based antimicrobial agent. Materials for fine powdery particles having a sphericity of 40 or more to be used in an external skin agent of the present invention can be either organic or inorganic.

Although harm to the human body caused by conventionally used compounds such as parabenes, benzalkonium chloride, banzetonium chloride, and chlorohexidine gluconate has been suggested, those compounds have been reluctantly used from urgent necessity because no alternative is available. Therefore, shift to an external skin agent of the present invention, which is safe to the human body, is significant.

An external skin agent of the present invention is effective in preventing coloring of silver zeolite, and this effect can also be applicable for silver apatite-based antimicrobial agents and silver aluminium silicate-based antimicrobial agents.

An external skin agent of the present invention is effective in preventing coloring of antimicrobial agent using silver ions. Additives of the abovementioned combination can be incorporated into a container or packaging material to be used for the external skin agent throughout or at a part in contact with the external skin agent in order to protect the contained external skin agent from bacterial or fungal contamination without coloring.

Examples of macromolecular tackiness agents to be used in the present invention include Geran gum, carrageenin, PVA, polyvinyl acetate, CMC, polyacrylamide, alginic acid, agar, polyacrylic acid, polymethacrylic acid, pectin, gelatin, and pullulan.

Examples of moisture-retaining agents include glycerin, diglyceride, polyglyceride, ethylene glycol, diethylene glycol, polyethylene glycol, propylene glycol, 1,3-butylene glycol, urea, and chitosan collagen.

As mentioned above, an external skin agent of the present invention is an effective agent containing a silver-based antimicrobial agent and compounds selected from bases of nucleic acid components, thiabendazole, and benzotriazole and having a coloring preventing effect. By incorporating additives of the abovementioned combination into a plastic container or packaging material to be used for the external skin agent throughout or partially, coloring of the container itself can be prevented and coloring of the contained external skin agent due to the effect of silver ions released from the container can also be prevented. In this case, bases to be admixed are preferably pyrimidine bases, thiabendazole or benzotriazole, and purine bases are not appropriate in terms of heat tolerance. The combination of the abovementioned additives of the present invention can be used in paper, gum, building materials, and the like other than plastics which are raw materials for containers or packaging.

As to an antimicrobial plastic composition of the present invention, examples of products to be contained in a container or packaging which is made using the antimicrobial plastic composition containing a silver-based antimicrobial agent and silver ion trapping agents at least as a part of its component include commonly used aerosols, powders, pressed powders, and creams, and in particular, cosmetics such as underarm deodorants, talcum powders, hair tonics, toothpastes, bath agents, toiletries (e.g., shampoos, rinses, cosmetics, creams, milky lotions, and soaps), rectal cleansing agents, and lady's cleansing agents.

As to an antimicrobial plastic composition of the present invention, the abovementioned combination of a silver-based antimicrobial agent and silver ion trapping agents is effective in brushes made of fiber in which the antimicrobial plastic composition is arranged in the sheath, synthetic resin brushes made of the antimicrobial plastic, textiles made of the antimicrobial plastic, and the like.

PE (polyethylene), PP (polypropylene), PET (polyethylene terephthalate), EVA (ethylene-vinyl acetate copolymer), polyurethane, nylon, vinyl chloride, and vinyl acetate can be used as plastic preforms to compose an antimicrobial plastic of the present invention. Containers and packaging are formed out of solid or spongy substances made of the abovementioned plastic preforms by ordinary molding methods. The abovementioned brushes and textiles are also produced by ordinary methods.

The present invention will be explained more specifically by the following examples.

EXAMPLE 1

A 200-ml bottle for cosmetics was produced by admixing PP (polypropylene) with 1% by weight Zeomic AJ-10N (silver zeolite, Sinanen Co., Ltd.), 0.3% by weight thymine, and 0.4% by weight uracil. An antiperspirant lotion was put into the bottle as a cosmetic and then stored.

After storing for 3 months, the PP container showed no coloring.

COMPARATIVE EXAMPLE 1

A 200-ml bottle for cosmetics was produced by admixing PP with 1% by weight Zeomic AJ-10N only in Comparative Example 1. The resulting container slightly turned yellow.

Further, an antiperspirant lotion was put into the container as a cosmetic. The container colored brown on the following day.

EXAMPLE 2

A packaging material comprising heat adhesive two layers was produced by admixing PE (polyethylene) with 1% by weight silver apatite and 0.8% by weight thiabendazole and laminating the resulting admixture on one side of a 100 µm PET film.

A wet tissue-like product in which a cleansing solution was infiltrated into nonwoven cloth was wrapped like a pillow with the packaging material. After storing for 6 months, neither the packaging material nor the content showed coloring.

COMPARATIVE EXAMPLE 2

A packaging material for Comparative Example 2 was produced by admixing PE with 1% by weight silver apatite and laminating the resulting admixture on a 100 µm PET film as described above. The content wrapped like a pillow with the packaging material of Comparative Example 2 turned yellow on the following day.

EXAMPLE 3

Urethane sponge for a body sponge was produced by admixing polyurethane with 1% by weight silver glass and 0.8% by weight thiabendazole. The body sponge of the present invention was impregnated with body soap for body cleansing and used for 3 months. As a result, an antimicrobial effect was attained absolutely without coloring.

COMPARATIVE EXAMPLE 3

In contrast, urethane sponge produced by admixing polyurethane with 1% by weight silver glass colored brown on the second day of use for body cleansing.

EXAMPLE 4

A brush for cosmetic use without coloring was produced by admixing nylon 6 with 1% by weight Zeomic AJ-10N (silver zeolite, Sinanen Co., Ltd.) and 1% by weight thiabendazole and spinning the resulting admixture into monofilaments for the brush. The product showed no coloring for more than 6 months.

COMPARATIVE EXAMPLE 4

A brush produced in a conventional manner by using an admixture only with Zeomic AJ-10N (supra) for spinning colored yellow immediately after production and further turned to brown, which made the product uneconomic and impractical.

EXAMPLE 5

Polyester fiber 75d36f was produced by admixing PET with 1% by weight Zeomic AJ-10N and 0.8% by weight thiabendazole. The resulting fiber for clothes bore scouring in a weaving process without changing color.

COMPARATIVE EXAMPLE 5

A product produced in a conventional manner by using an admixture only with Zeomic AJ-10N for spinning colored yellow immediately after production.

Thus, in regard to the conventional coloring problem caused by reaction of silver ions and components of contents of cosmetics, use of antimicrobial plastic compositions of the present invention could significantly prevent coloring caused by silver ions.

Further, the coloring preventing action by combination of the abovementioned silver-based antimicrobial agent with nucleic acid components or the like can be similarly exhibited in a container in which a plastic composition comprising these agents is arranged on the whole, inside or outside surface; in a packaging material into which the plastic composition is entirely or partially incorporated; in a brush formed with fiber in which the antimicrobial plastic composition is arranged in the sheath, in a synthetic resin brush made of the antimicrobial plastic, and in fiber made of the antimicrobial plastic.

The coloring prevention effect of the combination of the present invention was tested and confirmed in underarm deodorants, talcum powders, hair tonics, toothpastes, bath agents, cosmetics (astringent lotions), rectal cleansing agents, and the like.

EXAMPLE 6

Underarm Deodorant

Powder Spray

Example 6 of the Present Invention

| | |
|---|---|
| Aluminium chlorohydrate | 30.0% |
| Silicic acid anhydrate powdery particles | 25.0% |
| Isopropyl myristate | 22.0% |
| Dimethyl-polysiloxan | 15.0% |
| Sorbitan fatty acid ester | 6.0% |
| Zeomic AJ-10N (silver zeolite antimicrobial agent, trademark: Sinanen Co., Ltd.) | 1.0% |
| Guanine | 1.0% |

COMPARATIVE EXAMPLE 6

| | |
|---|---|
| Aluminium chlorohydrate | 30.0% |
| Silicic acid anhydride powdery granules | 25.0% |
| Isopropyl myristate | 22.0% |
| Dimethyl-polysiloxan | 15.0% |
| Sorbitan fatty acid ester | 6.0% |
| Zeomic AJ-10N (silver zeolite antimicrobial agent, trademark: Sinanen Co., Ltd.) | 1.0% |

In the underarm deodorant product of Comparative Example 6, the product colored itself yellow one day after production and stained underwear when used.

In the underarm deodorant product of Example 6 of the present invention, the product itself exhibited no coloring after an accelerated test at 40° C. for 3 months.

Further, the underarm deodorant of Example 6 of the present invention was revealed to be equally effective as a body deodorant as an underarm deodorant.

EXAMPLE 7

Talcum Powder

Example 7A of the Present Invention

| | |
|---|---|
| Talc | 92.0% |
| Zinc oxide | 3.0% |
| Magnesium stearate | 3.0% |
| Zeomic AW (silver zeolite antimicrobial agent, trademark: Sinanen Co., Ltd.) | 1.0% |
| Adenine | 0.5% |
| Guanine | 0.5% |

Example 7B of the Present Invention

| | |
|---|---|
| Talc | 82.0% |
| Zinc oxide | 3.0% |
| Magnesium stearate | 3.0% |
| Zeomic AW (silver zeolite antimicrobial agent, trademark: Sinanen Co., Ltd.) | 1.0% |
| Adenine | 0.5% |
| Guanine | 0.5% |
| Silica powder (sphericity: 70, particle diameter: 5-10 μm) | 10.0% |

COMPARATIVE EXAMPLE 7

| | |
|---|---|
| Talc | 93.0% |
| Zinc oxide | 3.0% |
| Magnesium stearate | 3.0% |
| Zeomic AW (silver zeolite antimicrobial agent, trademark: Sinanen Co., Ltd.) | 1.0% |

In the talcum power of Comparative Example 7, the product colored itself yellow one day after production and stained underwear when used as a baby powder.

In contrast, the product of Example 7A of the present invention exhibited no coloring even after an accelerated test at 40° C. for 3 months and revealed to be usable as a talcum powder having an antimicrobial activity without coloring yellow.

Further, in addition to the abovementioned effect, the talcum powder of Example 7B of the present invention dissolved rough feeling to the skin caused by silver-based antimicrobial agents and provided smooth and comfortable feeling.

EXAMPLE 8

Hair Tonic

Example 8 of the Present Invention

| | |
|---|---|
| Pantothenyl ethyl ether | 0.1% |
| Dl-α-Tocopherol acetate | 0.1% |
| 1-Menthol | 0.1% |
| Camphor | 0.1% |
| Capsicum tincture | 0.5% |
| PO-hardened castor oil | 0.5% |
| Pyridoxine dicaprylate | 0.05% |
| 1,3-Butylene glycol | 3.0% |
| Mulberry extract | 1.0% |
| Japanese angelica root extract | 0.2% |
| Placenta extract | 0.5% |
| Citric acid | 0.02% |
| Sodium citrate | 0.1% |
| Denatured alcohol | 30.0% |
| Novaron (registered trademark, silver zirconium phosphate, Toagosei Co., Ltd.) | 0.8% |
| Cytosine | 0.4% |
| Thymine | 0.4% |
| Purified water | 62.13% |

COMPARATIVE EXAMPLE 8

| | |
|---|---|
| Pantothenyl ethyl ether | 0.1% |
| Dl-α-Tocophenyl acetate | 0.1% |
| Menthol | 0.1% |
| Camphor | 0.1% |
| Capsicum tincture | 0.5% |
| PO-hardened castor oil | 0.5% |
| Pyridoxine dicaprylate | 0.05% |
| 1,3-BG | 3.0% |
| Mulberry extract | 1.0% |
| Japanese angelica root extract | 0.2% |
| Placenta extract | 0.5% |
| Citric acid | 0.02% |
| Sodium citrate | 0.1% |
| Denatured alcohol | 30.0% |
| Silver zirconium phosphate (registered trademark, silver zirconium phosphate, Toagosei Co., Ltd.) | 0.8% |
| Purified water | 62.93% |

The hair tonic of Comparative Example 8 colored yellow one day after production and the coloring increased with time.

In contrast, the hair tonic of Example 8 of the present invention exhibited no coloring even after an accelerated test at 40° C. for 3 months.

Further, in addition to the hair tonic effect, the hair tonic of Example 8 of the present invention was effective in stopping itchiness on the scalp.

EXAMPLE 9

Toothpaste

Example 9 of the Present Invention

| | |
|---|---|
| Calcium secondary phosphate, dihydrate | 45.0% |
| Silicic acid anhydride | 2.0% |
| Glycerin | 15.0% |
| CMC | 1.0% |
| Sodium lauryl sulfate | 1.5% |
| Saccharin sodium | 0.5% |
| Zeomic AW (silver zeolite antimicrobial agent, registered trademark; Sinanen Co., Ltd.) | 1.0% |
| Uracil | 0.4% |
| Guanine | 0.3% |
| Purified water | 33.7% |

COMPARATIVE EXAMPLE 9

| | |
|---|---|
| Calcium secondary phosphate, dihydrate | 45.0% |
| Silicic acid anhydride | 2.0% |
| Glycerin | 15.0% |
| CMC | 1.0% |
| Sodium lauryl sulfate | 1.5% |
| Saccharin sodium | 0.1% |
| Zeomic AW (silver zeolite antimicrobial agent, registered trademark; Sinanen Co., Ltd.) | 1.0% |
| Purified water | 34.4% |

The toothpaste of Comparative Example 9 itself colored yellow already one day after production and the coloring was accelerated with time.

The toothpaste product of Example 9 of the present invention exhibited no coloring even after an accelerated test at 40° C. for 3 months.

Further, it was confirmed that the toothpaste of the present invention is useful as effective toothpaste for removing bad breath and preventing dental caries, pyorrhea alveolaris and pneumonia of bedridden patients.

EXAMPLE 10

Bath Agent

Example 10 of the Present Invention

| | |
|---|---|
| Sodium sulfate | 45.0% |
| Sodium hydrogencarbonate | 22.5% |
| Sodium carbonate | 8.0% |
| Succinic acid | 22.0% |
| Apasider (registered trademark, silver apatite; Sangi Co., Ltd.) | 6.0% |
| Adenosine diphosphate | 1.0% |

COMPARATIVE EXAMPLE 10

| | |
|---|---|
| Sodium sulfate | 45.0% |
| Sodium hydrogencarbonate | 23.5% |
| Sodium carbonate | 8.0% |
| Succinic acid | 22.0% |
| Silver apatite (registered trademark, silver apatite; Sangi Co., Ltd.) | 1.5% |

Bath water colored with the lapse of time when the bath agent of Comparative Example 10 was added into water in a tub.

In contrast, when the bath agent of Example 10 was added to water in the bath, coloring was exhibited neither in the bath water nor on the body after bathing. The coloring preventing action was effective on the following day so that no coloring was exhibited in the bath water and the remaining water could be used for washing without staining the laundry.

EXAMPLE 11

Cosmetic

Astringent Lotion

Example 11A of the Present Invention

| | |
|---|---|
| Dipropylene glycol | 1.0% |
| Sorbit | 1.0% |
| POE (20) oleyl alcohol ether | 1.0% |
| Zinc phenol sulfonate | 0.2% |
| Citric acid | 0.1% |
| Zeomic AW (registered trademark, silver zeolite antimicrobial agent; Sinanen Co., Ltd.) | 1.0% |
| Guanine | 0.4% |
| Adenosine monophosphate | 0.4% |
| Purified water | 95.1% |

Example 11B of the Present Invention

| | |
|---|---|
| Dipropylene glycol | 1.0% |
| Sorbit | 1.0% |
| POE (20) oleyl alcohol ether | 1.0% |
| Zinc phenol sulfonate | 0.2% |
| Citric acid | 0.1% |
| Zeomic AW | 1.0% |
| Guanine | 0.4% |
| Adenosine monophosphate | 0.4% |
| Organic silicone powder (sphericity: 80, particle diameter: 10-60 μm) | 5.0 |
| Purified water | 90.1% |

Comparative Example 11 of the Present Invention

| | |
|---|---|
| Dipropylene glycol | 1.0% |
| Sorbit | 1.0% |
| POE (20) oleyl alcohol ether | 1.0% |
| Zinc phenol sulfonate | 0.2% |
| Citric acid | 0.1% |
| Zeomic AW (registered trademark, silver zeolite antimicrobial agent; Sinanen Co., Ltd.) | 1.0% |
| Purified water | 95.7% |

The astringent lotion of Comparative Example 11 itself colored yellow one day after production.

In contrast, the product of Example 11A of the present invention itself exhibited no coloring after an accelerated test at 40° C. for 3 months, and absolutely no coloring occurred when applied on the skin.

Further, in addition to the abovementioned coloring preventing effect, the astringent lotion of Example 11B of the present invention completely dissolved rough feeling to the skin caused by zeolite, by the use of globular powdery particles.

EXAMPLE 12

Rectal Cleansing Agent

Example 12A of the Present Invention

| | |
|---|---|
| N-Lauryl-L-glutamic acid-triethanolamine (30%) | 0.1% |
| Triethanolamine myristate | 0.1% |
| Propylene glycol | 5.0% |
| Zeomic AW (registered trademark, silver zeolite antimicrobial agent; Sinanen Co., Ltd.) | 1.5% |
| Adenosine triphosphate | 1.0% |
| Purified water | 92.3% |

Example 12B of the Present Invention

| | |
|---|---|
| N-Lauryl-L-glutamic acid-triethanolamine (30%) | 0.1% |
| Triethanolamine myristate | 0.1% |
| Propylene glycol | 5.0% |
| Zeomic AW (registered trademark, silver zeolite antimicrobial agent; Sinanen Co., Ltd.) | 1.5% |
| Adenosine triphosphate | 1.0% |
| Nylon powder (sphericity: 70, particle diameter: 5-50 μm) (Nylon Powder-SP-500, Toray Co., Ltd.) | 4.0% |
| Purified water | 88.3% |

COMPARATIVE EXAMPLE 12

| | |
|---|---|
| N-Lauryl-L-glutamic acid-triethanolamine (30%) | 0.1% |
| Triethanolamine myristate | 0.1% |
| Propylene glycol | 5.0% |
| Zeomic AW (registered trademark, silver zeolite antimicrobial agent; Sinanen Co., Ltd.) | 1.5% |
| Purified water | 93.3% |

The rectal cleansing agent of Comparative Example 12 colored yellow one day after production.

The product of Example 12A of the present invention exhibited no coloring even after an accelerated test at 40° C. for 3 months. Further, the product of Example 12B of the present invention exhibited absolutely no rough feeling to the skin similarly as in Example 11.

Further, a similar coloring preventing effect was attained in lady's cleansing agents using a similar formula.

EXAMPLE 13

Talcum Powder

| | |
|---|---|
| Talc | 92.0% |
| Zinc oxide | 3.0% |
| Magnesium stearate | 3.0% |
| Zeomic AW (silver zeolite antimicrobial agent, trademark: Sinanen Co., Ltd.) | 1.0% |
| Potassium iodide | 1.0% |

The talcum power of Example 13 exhibited no coloring even after an accelerated test at 40° C. for 3 months and was usable as a talcum powder having an antimicrobial activity without coloring yellow, while a talcum powder without potassium iodide colored yellow one day after production and stained underwear when used as a baby powder.

Thus, in external skin agents of the present invention, coloring caused by silver ions is markedly prevented by using 1 to 100 parts by weight of components selected from the abovementioned purine bases or pyrimidine bases of nucleic acid components or free bases thereof, or thiabendazole to 100 parts by weight of silver zeolite, as silver ion trapping components.

Further, in external skin agents of the present invention, coloring caused by silver ions is markedly prevented by using potassium iodide and silver zeolite, as silver ion trapping components.

Furthermore, the coloring prevention effect can be improved and at the same time rough feeling to the skin can be dissolved by admixing 10 to 1000 parts by weight of fine powdery particles having a sphericity of 40 or more and incorporating the resulting admixture into the external skin agents at a ratio of about 0.01 to 10% by weight in total of the 2 to 3 components.

Furthermore, the combination of the abovementioned agents is equally effective when they are contained in the entirety or a part of containers or packaging materials for external skin agents as when they are added to the external skin agents themselves.

In the present invention, examples of external skin agents in which a coloring prevention effect can be attained include underarm deodorants, talcum powders, hair tonics, toothpastes, bath agents, toiletries (e.g., shampoos, rinses, cosmetics, milky lotions, and soaps), rectal cleansing agents, and lady's cleansing agents.

EXAMPLE 14

Cotton nonwoven cloth having a base weight of 40 g/m was cut into 150×200 cm sheets. The sheets were folded, piled into 20 layers and impregnated with a liquid of formula 1 or comparative formula at a ratio of 300% by weight, immediately after which each sheet was airtightly pillow-packed.

The wet tissue of the present invention and the comparative product were subjected to an acceleration test for coloring to judge coloring preventing effect.

Formula 1 (Product of the Present Invention)

| | |
|---|---|
| Zeomic AW* | 0.10% by weight |
| Propylene glycol | 7.00% |
| Adenine | 0.02% |
| Guanine | 0.02% |
| Purified water | up to 100% by weight |

*Zeomic AW: (registered trademark, Sinanan Co., Ltd., silver zeolite antimicrobial agent)

Formula 2 (Comparative Product)

| | |
|---|---|
| Zeomic AW | 0.10% by weight |
| Propylene glycol | 7.00% |
| Purified water | up to 100% by weight |

The wet tissue obtained according to the comparative formula colored yellow one day after production. The abovementioned contained solution itself slightly colored, but it was markedly colored when impregnated into the nonwoven cloth.

In contrast, the wet tissue obtained according to the formula 1 of the present invention exhibited no coloring even after an acceleration test at 40° C. for 3 months.

When the body was wiped using the wet tissue of the present invention with absolutely no coloring, an excellent deodorant effect was shown by removing the body odor.

EXAMPLE 15

Components comprising the following formulae were applied on paper (35 g/m²) manufactured from 40% by weight of rayon and 60% by weight of pulp and made into paste-type cosmetics, on which a separate paper was placed for use on the face. The abovementioned paste-type cosmetics according to the formula of the present invention and the control formula were subjected to an acceleration test for coloring to evaluate long-term stability and test antimicrobial action.

Formula 3 (Product of the Present Invention)

| | |
|---|---|
| Sodium polyacrylate | 7.00% by weight |
| Aluminium hydroxide | 0.15 |
| Glycerin | 10.00% |
| Zeomic AW | 0.09% |
| Cytosine | 0.01% |
| Thymine | 0.01% |
| Uracil | 0.01% |
| Purified water | up to 100% by weight |

Formula 4 (Comparative Product)

| | |
|---|---|
| Sodium polyacrylate | 7.00% by weight |
| Aluminium hydroxide | 0.15% |
| Glycerin | 10.00% |
| Zeomic AW | 0.09% |
| Purified water | up to 100% by weight |

The paste-type cosmetic obtained according to the comparative formula colored brown one day after production, while the product of the present invention exhibited no coloring even after an acceleration test at 40° C. for 3 months.

When a sheet made of nonwoven cloth or the like was impregnated with an aqueous medium, marked coloring was exhibited; however, the abovementioned coloring was completely prevented.

EXAMPLE 16

Nonwoven cloth comprising 70% by weight cotton and 30% by weight PP and having a base weight of 45 g/m² was cut into 150×200 cm sheets and impregnated with a deodorant liquid of the present invention (formula 5) or comparative product (formula 6) by pouring at a ratio of 300% by weight of the nonwoven cloth, after which each sheet was airtightly pillow-packed. Coloring of the product of the present invention and the comparative product was observed.

Formula 5 (Product of the Present Invention)

| | |
|---|---|
| Aluminium chlorohydrate | 10.0% by weight |
| Absolute ethyl alcohol | 50.0% |
| 1,3-Buthylene glycol | 3.0% |
| Zeomic AW | 1.0% |
| RNA | 0.5% |
| Purified water | 35.5% |

Formula 6 (Comparative Product)

| | |
|---|---|
| Aluminium chlorohydrate | 10.0% by weight |
| Absolute ethyl alcohol | 50.0% |
| 1,3-Buthylene glycol | 3.0% |
| Zeomic AW | 1.0% |
| Purified water | 36.0% |

The comparative product (formula 6) colored yellow one day after production but the product of the present invention exhibited no coloring even after an acceleration test at 40° C.

for 3 months. The product of the present invention was effective as a deodorant to prevent body odor.

Further, an antimicrobial test was carried out with paste-type cosmetics of the present invention.

In the antimicrobial test, the paste-type cosmetics were cut into 50×50 mm pieces, placed on a medium composed of 0.5% meat extract, 1.0% peptone (potato extract), 0.5% salt, 1.5% agar, 96.5% purified water with inoculated test microorganisms ($3\times10^5$), i.e., strains of *E. coli, S. aureus*, and *P. aeruginosa*, and incubated at a culture temperature of 37° C. for 24 hours. Both the product of the present invention and the comparative product showed the bacterial count of 100 or less, and thus antimicrobial action according to the method of present invention was confirmed.

Silver zeolite-based antimicrobial agents have an excellent activity to prevent underarm and body odor and are effective to fight against acne bacteria. They are safe in use on the body but cause coloring on the skin or clothes, which limited their use. In the present invention, sheet-like cosmetics such as wet tissues and paste-type products without coloring problems can be obtained by using an admixture of silver zeolite antimicrobial agents with one or more kinds of compounds, which has a silver ion trapping effect on silver zeolite antimicrobial agents, selected from purine bases, pyrimidine bases and thiabendazole.

In the present invention, the coloring preventing effect on silver zeolite agents attained by using one or more compounds selected from purine bases, pyrimidine bases and thiabendazole is not limited to sheet-type cosmetics but also exhibited in other cosmetics in which the silver zeolite antimicrobial agents are used.

The present invention comprises the following embodiments.

1) An antimicrobially-treated material which has a coloring preventing function and is in contact with water or moisture or contains water, comprising (A) a silver-based antimicrobial agent which dissociates silver ions in a water system and (B) a silver ion trapping agent for trapping silver ions comprising one or more kinds of compounds selected from the group consisting of purine bases, pyrimidine bases, thiabendazole, and potassium iodide, wherein a ratio of (A)/(B) is 1/1 to 100/1 by weight.

2) An antimicrobially-treated material as described in item 1, which comprises a plastic preform, wherein said component (A) and said component (B) are contained at a ratio of 0.05 to 5.0% by weight in total, relative to 100% by weight of the plastic preform.

3) An antimicrobially-treated material as described in item 1, wherein said silver-based antimicrobial agent is selected from the group consisting of silver zeolite, silver apatite, silver zirconium phosphate, and silver glass.

4) An antimicrobially-treated material as described in item 1, which further contains (C) globular powdery particles having a sphericity of 40 or less.

5) An antimicrobially-treated material as described in item 4, wherein said component (C) is contained at a ratio of (A)/(C)=0.1 to 10 by weight.

6) An antimicrobially-treated material as described in item 1, wherein said component (A) and said component (B) are incorporated into a sheet base with an aqueous medium.

7) An antimicrobially-treated material as described in item 1, wherein said purine bases or pyrimidine bases are free bases or components of DNA or RNA.

8) An antimicrobially-treated material as described in item 6, wherein 0.02 to 3.0% by weight said component (A) and 0.0002 to 3.0% by weight said component (B) are integrated through 50 to 300% by weight said aqueous medium into 100% by weight said sheet base.

9) An antimicrobial plastic composition having a coloring preventing function, which comprises (A) a silver-based antimicrobial agent and (B) one or more kinds of compounds selected from the group consisting of purine bases, pyrimidine bases, thiabendazole, and potassium iodide.

10) An antimicrobial plastic composition as described in item 9, wherein (A) 100 parts by weight of silver-based antimicrobial agent and (B) 1 to 100 parts by weight of one or more kinds of compounds selected from the group consisting of purine bases, pyrimidine bases, thiabendazole, and potassium iodide are contained at a ratio of 0.05 to 5.0% by weight in total, relative to 100% by weight plastic preform.

11) An antimicrobial plastic composition as described in item 9, wherein said silver-based antimicrobial agent is selected from the group consisting of silver zeolite, silver apatite, silver zirconium phosphate, and silver glass.

12) An antimicrobial plastic composition as described in item 10, wherein said plastic preform is a solid or porous composite of one or more kinds of compounds selected from the group consisting of PE, PP, PET, polyurethane, nylon, vinyl chloride, vinyl acetate, and EVA.

13) An antimicrobial plastic composition having a coloring preventing function, wherein the antimicrobial plastic composition as described in item 9 is arranged in the whole or on the outer surface or inner surface of a container or a packaging material.

14) An antimicrobial plastic container having a coloring preventing function, wherein the antimicrobial plastic composition as described in item 9 is arranged in the whole or on the outer surface or inner surface of a container by an in-mold forming or surface treatment.

15) An antimicrobial plastic packaging material having a coloring preventing function, wherein the antimicrobial plastic composition described in 9 is arranged in one or more layers of a single-layer or multiple-layer film.

16) An antimicrobial plastic brush having a coloring preventing function, wherein the antimicrobial plastic composition described in item 9 is a brush made of synthetic fiber.

17) An antimicrobial plastic brush having a coloring prevention function, wherein the antimicrobial plastic composition described in item 9 is arranged in the sheath of sheath-core fiber.

18) Antimicrobial plastic fiber having a coloring preventing function, wherein the antimicrobial plastic composition described in item 9 is synthetic fiber.

19) An external skin agent having a coloring preventing function, which comprises (A) a silver-based antimicrobial agent and (B) one or more kinds of compounds selected from the group consisting of purine bases, pyrimidine bases, thiabendazole, and potassium iodide.

20) An external skin agent as described in item 19, which further comprises (C) globular powdery particles having a sphericity of 40 or more.

21) An external skin agent as described in item 19, wherein said purine bases or pyrimidine bases are free bases or components of DNA or RNA.

22) An external skin agent as described in item 19, which comprises 100 parts by weight of (A) a silver-based antimicrobial agent and 1 to 100 parts by weight of (B) one or more kinds of compounds selected from the group consisting of purine bases, pyrimidine bases, thiabendazole, and potassium iodide.

23) An external skin agent as described in item 19, which comprises 100 parts by weight of (A) a silver-based antimicrobial agent, 1 to 100 parts by weight of (3) one or more kinds of compounds selected from the group consisting of purine bases, pyrimidine bases, thiabendazole, and potassium iodide and 10 to 1000 parts by weight of (C) globular powdery particles having a sphericity of 40 or more.

24) An external skin agent as described in item 19, which comprises (A) a silver-based antimicrobial agent, (B) one or more kinds of compounds selected from the group consisting of purine bases, pyrimidine bases, thiabendazole, and potassium iodide and (C) globular powdery particles having a sphericity of 40 or more at a ratio of 0.05 to 5.0% by weight in total in the external skin agent.

25) An external skin agent as described in item 19, wherein said silver-based antimicrobial agent is selected from the group consisting of silver zeolite, silver apatite, silver zirconium phosphate, silver glass, and inorganic coating silver oxide.

26) A sheet-like cosmetic having a coloring preventing function, wherein (A) a silver-based antimicrobial agent and (B) one or more kinds of compounds selected from the group consisting of purine bases, pyrimidine bases, thiabendazole, and potassium iodide are retained in a sheet base with an aqueous medium.

27) A sheet-like cosmetic as described in item 26, wherein said purine bases or pyrimidine bases are free bases or components of DNA or RNA.

28) A sheet-like cosmetic as described in item 26, wherein 0.02 to 3.0% by weight said component (A) and 0.0002 to 3.0% by weight said component (B) are integrated through 50 to 300% by weight said aqueous medium into 100% by weight said sheet base.

29) A sheet-like cosmetic as described in item 26, which comprises 100 parts by weight of (A) a silver-based antimicrobial agent and 1 to 100 parts by weight of (B) one or more kinds of compounds selected from the group consisting of purine bases, pyrimidine bases, thiabendazole, and potassium iodide.

30) A sheet-like cosmetic as described in item 26, wherein said aqueous medium is selected from the group consisting of hair tonics, purified water, deodorant lotions, oral lotions, body lotions, and facial lotions.

31) A sheet-like cosmetic as described in item 26, wherein said sheet base is selected from the group consisting of nonwoven cloth, paper and porous sheets.

32) A sheet-like cosmetic as described in item 26, wherein (A) a silver-based antimicrobial agent and (B) one or more kinds of compounds selected from the group consisting of purine bases, pyrimidine bases, thiabendazole, and potassium iodide are directly added to a spinning material of nonwoven cloth which composes the sheet base or directly incorporated into a porous sheet which composes the sheet base.

33) A sheet-like cosmetic as described in item 26, wherein the sheet-like cosmetic is a wet tissue which is treated for coloring prevention.

34) A sheet-like cosmetic as described in item 26, wherein the sheet-like cosmetic is a paste-type cosmetic which is treated for coloring prevention.

35) A method of preventing coloring of an antimicrobially-treated material having contact with water or containing water, wherein (A) a silver-based antimicrobial agent which dissociates silver ions in the water system and (B) a silver ion trapping agent comprising one or more kinds of compounds selected from the group consisting of purine bases, pyrimidine bases, thiabendazole, and potassium iodide are mixed at a ratio of (A)/(B)=1 to 100 by weight.

36) A method of preventing coloring of an antimicrobially-treated material as described in item 35, wherein said component (A) and said component (B) are contained at a ratio of 0.05 to 5.0% by weight in total, relative to 100% by weight plastic preform.

37) A method of preventing coloring of an antimicrobially-treated material as described in item 35, wherein said silver-based antimicrobial agent is selected from the group consisting of silver zeolite, silver apatite, silver zirconium phosphate, and silver glass.

38) A method of preventing coloring of an antimicrobially-treated material as described in item 35, wherein the material further contains (C) globular powdery particles having a sphericity of 40 or more.

39) A method of preventing coloring of an antimicrobially-treated material as described in item 38, wherein said component (C) is contained at a ratio of (A)/(C)=0.1 to 10 by weight.

40) A method of preventing coloring of an antimicrobially-treated material as described in item 35, wherein said component (A) and said component (B) are incorporated into a sheet base with a water medium.

41) A method of preventing coloring of an antimicrobially-treated material as described in item 35, wherein said purine bases or pyrimidine bases are free bases or components of DNA or RNA.

42) A method of preventing coloring of an antimicrobially-treated material as described in item 40, wherein 0.02 to 3.0% by weight said component (A) and 0.0002 to 3.0% by weight said component (B) are integrated through 50 to 300% by weight said aqueous medium into 100% by weight said sheet base.

What is claimed is:

1. A method of inhibiting coloring of an antimicrobially-treated plastic preform having contact with water or containing water, comprising:
   providing a plastic preform that can develop undesired coloring due to the effect of silver ions when admixed with an aqueous medium in the presence of a silver-based antimicrobial agent which dissociates silver ions in the aqueous medium;
   providing (A) a silver-based antimicrobial agent which dissociates silver ions in the aqueous medium;
   providing (B) a silver ion trapping agent comprising adenine, guanine, cytosine, thymine, and/or uracil in free base form; and
   mixing and dispersing (A) and (B) into the plastic preform; wherein (1) the ratio of (A)/(B) is 1/1 to 100/1 by weight, (2) (A) and (B) are contained at a ratio of 0.05 to 5.0% by weight in total, relative to 100% by weight of said plastic preform, and (3) said silver-based antimicrobial agent is selected from the group consisting of silver zeolite, silver apatite, silver zirconium phosphate, and silver glass;
   whereby said undesired coloring of the antimicrobially-treated plastic preform is inhibited.

2. The method according to claim 1, wherein the plastic preform is a solid or porous composite of one or more kinds of compounds selected from the group consisting of polyethylene (PE), polypropylene (PP), polyethylene terephthalate (PET), polyurethane, nylon, vinyl chloride, vinyl acetate, and ethylene-vinyl acetate copolymer (EVA).

3. A method of inhibiting coloring of an antimicrobially-treated sheet-shaped material with an aqueous medium, comprising:
   providing a sheet-shaped material with an aqueous medium that can develop undesired coloring due to the effect of silver ions when admixed with an aqueous medium in the presence of a silver-based antimicrobial agent which dissociates silver ions in the aqueous medium;

providing (A) a silver-based antimicrobial agent which dissociates silver ions in the aqueous medium;

providing (B) a silver ion trapping agent comprising adenine, guanine, cytosine, thymine, and/or uracil in free base form; and mixing and dispersing (A) and (B) into the sheet-shaped material with an aqueous medium;

wherein (1) the ratio of (A)/(B) is 1/1 to 100/1 by weight, (2) the component (A), the component (B), and the aqueous medium are used in an amount of 0.02 to 3.0% by weight, 0.0002 to 3.0% by weight, and 50 to 300% by weight, respectively, per 100% by weight of the sheet-shaped material, and (3) said silver-based antimicrobial agent is selected from the group consisting of silver zeolite, silver apatite, silver zirconium phosphate, and silver glass;

whereby said undesired coloring of the antimicrobially-treated plastic sheet-shaped material with an aqueous medium is inhibited.

4. The method according to claim 3, wherein the aqueous medium is selected from the group consisting of hair tonics, purified water, deodorant lotions, oral lotions, body lotions, and facial lotions.

5. The method according to claim 3, wherein the sheet-shaped material is selected from the group consisting of non-woven cloth, paper and porous sheets.

6. The method according to claim 3, wherein the dispersion step comprises adding the components (A) and (B) to a spinning material of nonwoven cloth which composes the sheet-shaped material.

7. The method according to claim 3, where the dispersion step comprises incorporating the components (A) and (B) into a porous sheet which composes the sheet-shaped material.

* * * * *